United States Patent
Sukegawa et al.

(10) Patent No.: US 9,679,820 B2
(45) Date of Patent: Jun. 13, 2017

(54) EVALUATION METHOD OF DEVICE WAFER

(71) Applicant: DISCO CORPORATION, Tokyo (JP)

(72) Inventors: Naoya Sukegawa, Tokyo (JP); Seiji Harada, Tokyo (JP)

(73) Assignee: Disco Corporation, Tokyo (JP)

( * ) Notice: Subject to any disclaimer, the term of this patent is extended or adjusted under 35 U.S.C. 154(b) by 171 days.

(21) Appl. No.: 14/752,155

(22) Filed: Jun. 26, 2015

(65) Prior Publication Data

US 2015/0377779 A1 Dec. 31, 2015

(30) Foreign Application Priority Data

Jun. 27, 2014 (JP) .................................. 2014-132279

(51) Int. Cl.
*G01N 21/55* (2014.01)
*H01L 21/66* (2006.01)
*G01N 21/95* (2006.01)

(52) U.S. Cl.
CPC .......... *H01L 22/12* (2013.01); *G01N 21/9501* (2013.01); *G01N 2201/06113* (2013.01)

(58) Field of Classification Search
CPC ................... H01L 22/12; G01N 21/55; G01N 2201/06113

USPC ............................................. 250/216; 451/73
See application file for complete search history.

(56) References Cited

U.S. PATENT DOCUMENTS 8,357,592 B2 * 1/2013 Kurita ................... H01L 21/268
257/E21.318
9,281,197 B2 * 3/2016 Kurita

FOREIGN PATENT DOCUMENTS

JP 2009-094326 4/2009

* cited by examiner

*Primary Examiner* — Seung C Sohn
(74) *Attorney, Agent, or Firm* — Greer Burns & Crain Ltd.

(57) ABSTRACT

An evaluation method of a device wafer on which plural devices are formed on a front surface and inside which a gettering layer is formed is provided. In the evaluation method, electromagnetic waves are radiated toward a back surface of the device wafer and excitation light is radiated to generate excess carriers. Furthermore, the gettering capability of the gettering layer formed in the device wafer is determined based on the damping time of reflected electromagnetic waves.

4 Claims, 4 Drawing Sheets

EVALUATION METHOD OF DEVICE WAFER

BACKGROUND OF THE INVENTION

Field of the Invention

The present invention relates to an evaluation method for evaluating the gettering capability of a device wafer on which plural devices are formed on a surface.

Description of the Related Art

In small-size, light-weight electronic apparatus typified by mobile phones, a device chip having a device such as an IC is an essential configuration. The device chip is manufactured by partitioning a surface of a wafer composed of a material such as silicon by plural planned dividing lines called streets and forming a device in each region and then dividing the wafer along the streets, for example.

In recent years, there are increasing opportunities to process a wafer on which devices have been formed (hereinafter, device wafer) into a thin wafer for the purpose of size reduction, weight reduction, and so forth of the device chip. However, for example when the device wafer is polished to be thinned to 100 μm or thinner, the gettering effect to suppress the movement of metal elements harmful to the devices is lowered and operation failure of the device frequently occurs. To solve this problem, a processing method in which a gettering layer that captures metal elements is formed in a device wafer has been proposed (refer to e.g. Japanese Patent Laid-open No. 2009-94326). In this processing method, the device wafer is ground under predetermined conditions to form the gettering layer including predetermined grinding distortion while keeping the flexural strength of the device wafer.

SUMMARY OF THE INVENTION

However, the gettering layer formed by the above-described processing method does not always exhibit favorable gettering capability. For evaluation of the gettering capability of the gettering layer, a method of actually contaminating the device wafer with metal elements can be used for example. However, in this case, it becomes impossible to obtain a device chip as a non-defective product. That is, with this evaluation method, the device wafer to become a product cannot be evaluated.

Therefore, an object of the present invention is to provide an evaluation method by which the gettering capability can be evaluated without contaminating a device wafer.

In accordance with an aspect of the present invention, there is provided an evaluation method of a device wafer on which a plurality of devices are formed on a front surface and inside which a gettering layer is formed. The evaluation method includes radiating electromagnetic waves toward a back surface of the device wafer and radiating excitation light to generate excess carriers, and determining the gettering capability of the gettering layer formed in the device wafer on the basis of the damping time of reflected electromagnetic waves.

In the present invention, the wavelength of the excitation light may be 904 nm and the device wafer in which the damping time is equal to or shorter than 94% of the damping time in a wafer inside which a gettering layer is not formed may be determined to have gettering capability.

Furthermore, in the present invention, the wavelength of the excitation light may be 532 nm and the device wafer in which the damping time is equal to or shorter than 75% of the damping time in a wafer inside which a gettering layer is not formed may be determined to have gettering capability.

Moreover, in the present invention, the wavelength of the excitation light may be 349 nm and the device wafer in which the damping time is equal to or shorter than 45% of the damping time in a wafer inside which a gettering layer is not formed may be determined to have gettering capability.

In the evaluation method of a device wafer according to the present invention, by utilizing such a relationship that the lifetime of the excess carriers generated by irradiation with the excitation light is shorter when the gettering capability of the gettering layer is higher, the gettering capability is evaluated on the basis of the damping time of the reflected electromagnetic waves equivalent to the lifetime of the carriers. Therefore, the gettering capability can be evaluated without having to contaminate the device wafer with metal elements differently from the evaluation method of the related art.

The above and other objects, features and advantages of the present invention and the manner of realizing them will become more apparent, and the invention itself will best be understood from a study of the following description and appended claims with reference to the attached drawings showing a preferred embodiment of the invention.

DETAILED DESCRIPTION OF THE PREFERRED EMBODIMENT

Figure 1A:
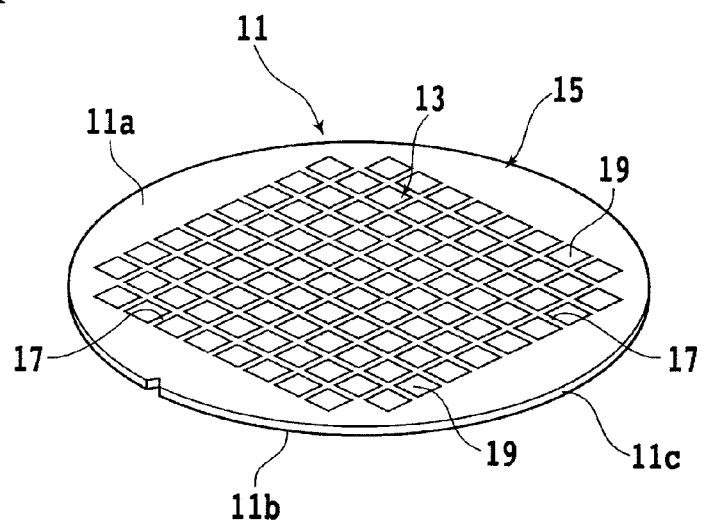
FIG. 1A is a perspective view schematically showing a device wafer before a gettering layer is formed.

An embodiment of the present invention will be described with reference to the accompanying drawings. First, a device wafer as a target of an evaluation method according to the present embodiment will be described. FIG. 1A is a perspective view schematically showing a device wafer before a gettering layer is formed. As shown in FIG. 1A, a device wafer 11 is formed of a disk-shaped wafer composed of a material such as silicon for example and a front surface 11a is divided into a device region 13 as a central region and a peripheral surplus region 15 surrounding the device region 13. The device region 13 is further partitioned into plural regions by streets (planned dividing lines) 17 arranged in a lattice manner and a device 19 such as an IC is formed in each region. Outer circumference 11c of the device wafer 11 is subjected to chamfering processing and is slightly rounded.

On the side of a back surface 11b of this device wafer 11, a gettering layer is formed by using a gettering layer forming method to be described next. The gettering layer forming method according to the present embodiment includes a protective member sticking step, a gettering layer forming step, and a stress removing step for example.

Figure 1B:
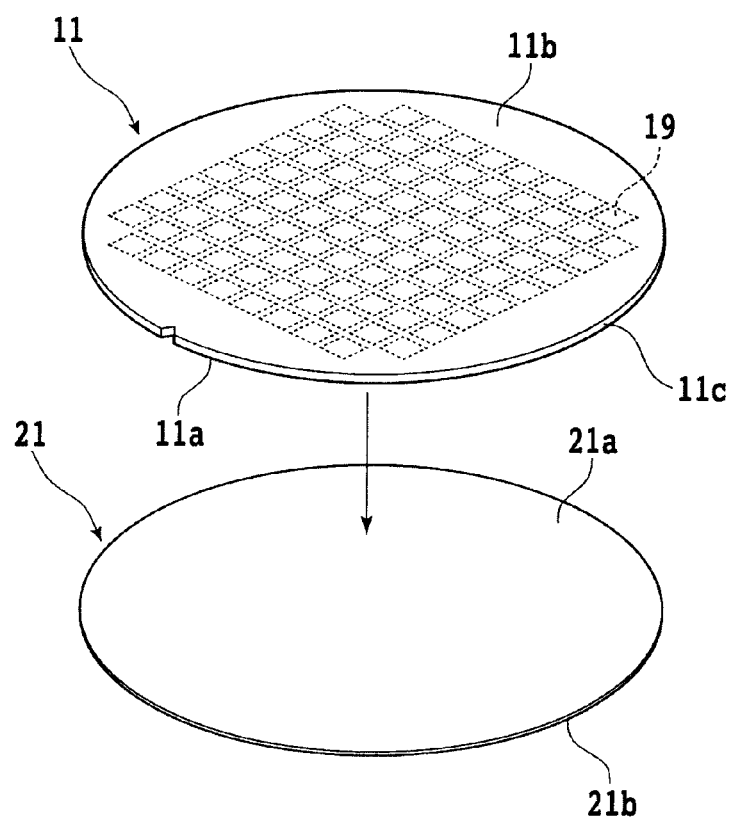
FIG. 1B is a perspective view schematically showing how a protective member is stuck to the front surface side of the device wafer.

First, the protective member sticking step of sticking a protective member to the side of the front surface 11a of the device wafer 11 is carried out. FIG. 1B is a perspective view schematically showing the protective member sticking step. As shown in 1B, a protective member 21 is formed into substantially the same disk shape as the device wafer 11 and an adhesive layer is provided on the side of the front surface 21a. As the protective member 21, e.g. an adhesive tape, a resin substrate, a semiconductor wafer, etc. can be used. In the protective member sticking step, the side of the front surface 11a of the device wafer 11 is made to face the side of the front surface 21a of the protective member 21 and the device wafer 11 and the protective member 21 are overlapped with each other. This causes the protective member 21 to be stuck to the side of the front surface 11a of the device wafer 11 with the intermediary of the adhesive layer.

Figure 2:
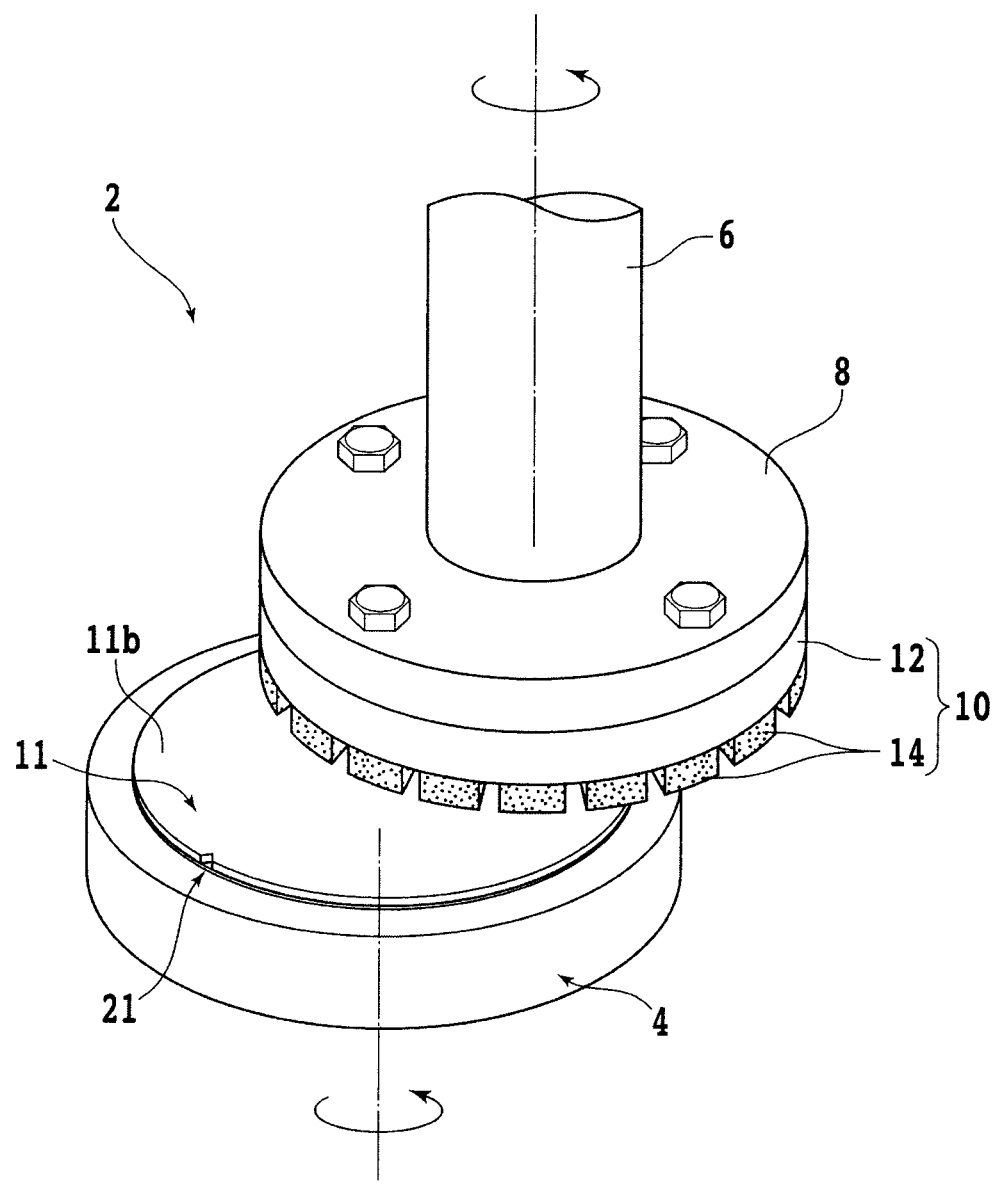
FIG. 2 is a perspective view schematically showing how the back surface side of the device wafer is ground to form the gettering layer.

Next, the gettering layer forming step of forming a gettering layer by grinding the side of the back surface 11b of the device wafer 11 is carried out. FIG. 2 is a perspective view schematically showing the gettering layer forming step. This gettering layer forming step is carried out by grinding apparatus 2 shown in FIG. 2 for example. The grinding apparatus 2 includes a chuck table 4 that holds the device wafer 11 by suction. This chuck table 4 is joined to a rotational drive source (not shown) such as a motor and rotates around a rotating axis extending along the vertical direction. The upper surface of the chuck table 4 serves as a holding surface to hold the device wafer 11 by suction. A negative pressure by a suction source (not shown) acts on the holding surface via a flow path formed inside the chuck table 4. A spindle 6 serving as a rotating shaft is supposed over the chuck table 4. This spindle 6 is moved up and down by an elevating mechanism (not shown). A rotational drive source (not shown) such as a motor is joined to the upper end side of the spindle 6. A wheel mount 8 having a disk shape is fixed to the lower end side of the spindle 6. A grinding wheel 10 having substantially the same diameter as the wheel mount 8 is mounted to the lower surface of the wheel mount 8. The grinding wheel 10 includes a wheel base 12 formed of a metal material such as stainless steel. Plural grinding stones 14 are fixed to the circular-ring-shaped lower surface of the wheel base 12 across the whole circumference. For example, the grinding stones 14 made by binding diamond abrasive grains whose grain size is at most 1 μm by a vitrified bond can be used. This can form a favorable gettering layer while keeping the flexural strength of the device wafer 11.

In the gettering layer forming step, first, the side of the back surface 21b of the protective member 21 stuck to the device wafer 11 is brought into contact with the holding surface of the chuck table 4 and the negative pressure by the suction source is made to act on the back surface 21b. Thereby, the device wafer 11 is held by suction by the chuck table 4 with the intermediary of the protective member 21 and the side of the back surface 11b is exposed to the upper side. Next, the grinding wheel 10 is lowered while the chuck table 4 and the spindle 6 are each rotated in a predetermined direction, and the grinding stones 14 are brought into contact with the side of the back surface 11b of the device wafer 11 while a grinding solution such as purified water is supplied. This can grind the side of the back surface 11b of the device wafer 11 and form a gettering layer 23 (see FIG. 4) including predetermined grinding distortion (stress). Conditions such as the rotating speed of the chuck table 4, the rotating speed of the spindle 6, the grinding feed rate (lowering rate) of the grinding wheel 10, the rate of supply of the grinding solution are adjusted in ranges suitable for the formation of the gettering layer 23. For example, it is preferable to adjust these conditions in the following ranges: 100 (rpm) to 400 (rpm) about the rotating speed of the chuck table 4; 1000 (rpm) to 6000 (rpm) about the rotating speed of the spindle 6; 0.05 (μm/s) to 0.5 (μm/s) about the grinding feed rate (lowering rate) of the grinding wheel 10; and 2 (L/min) to 10 (L/min) about the rate of supply of the grinding solution.

Figure 3:
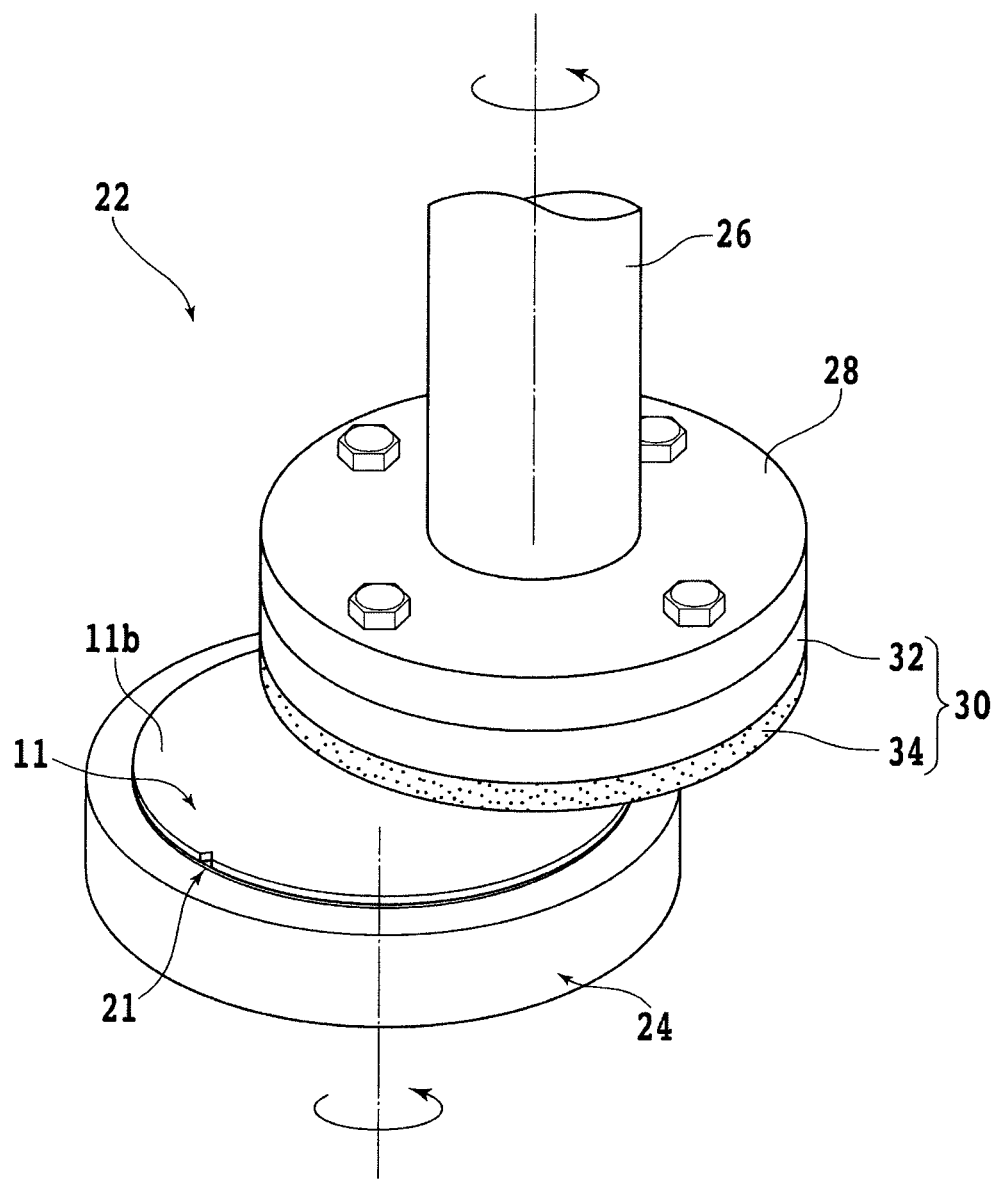
FIG. 3 is a perspective view schematically showing how the back surface side of the device wafer is polished to partly remove grinding distortion (stress)

Next, the stress removing step of polishing (typically CMP) the side of the back surface 11b of the device wafer 11 to partly remove the grinding distortion (stress) of the gettering layer 23 is carried out. FIG. 3 is a perspective view schematically showing the stress removing step. This stress removing step is carried out by polishing apparatus 22 shown in FIG. 3 for example. The configuration of the polishing apparatus 22 is similar to that of the grinding apparatus 2. Specifically, the polishing apparatus 22 includes a chuck table 24 that holds the device wafer 11 by suction. A spindle 26 serving as a rotating shaft is supposed over the chuck table 24. A wheel mount 28 having a disk shape is fixed to the lower end side of the spindle 26. A polishing wheel 30 having substantially the same diameter as the wheel mount 28 is mounted to the lower surface of the wheel mount 28. The polishing wheel 30 includes a wheel base 32 formed of a metal material such as stainless steel. A polishing pad 34 having a disk shape is fixed to the lower surface of the wheel base 32.

In the stress removing step, first, the side of the back surface 21b of the protective member 21 stuck to the device wafer 11 is brought into contact with the holding surface of the chuck table 24 and a negative pressure by a suction source is made to act on the back surface 21b. Thereby, the device wafer 11 is held by suction by the chuck table 24 with the intermediary of the protective member 21 and the side of the back surface 11b is exposed to the upper side. Next, the polishing wheel 30 is lowered while the chuck table 24 and the spindle 26 are each rotated in a predetermined direction, and the polishing pad 34 is brought into contact with the side of the back surface 11b of the device wafer 11 while a polishing solution is supplied. This can polish the side of the back surface 11b of the device wafer 11 and partly remove the grinding distortion (stress) of the gettering layer 23. In this stress removing step, the side of the back surface 11b of the device wafer 11 is so polished that a certain level of grinding distortion remains. This can keep the flexural strength of the device wafer 11 while ensuring the gettering capability. In e.g. the case in which the grinding distortion of the device wafer 11 does not need to be removed, the stress removing step can be omitted.

Figure 4:
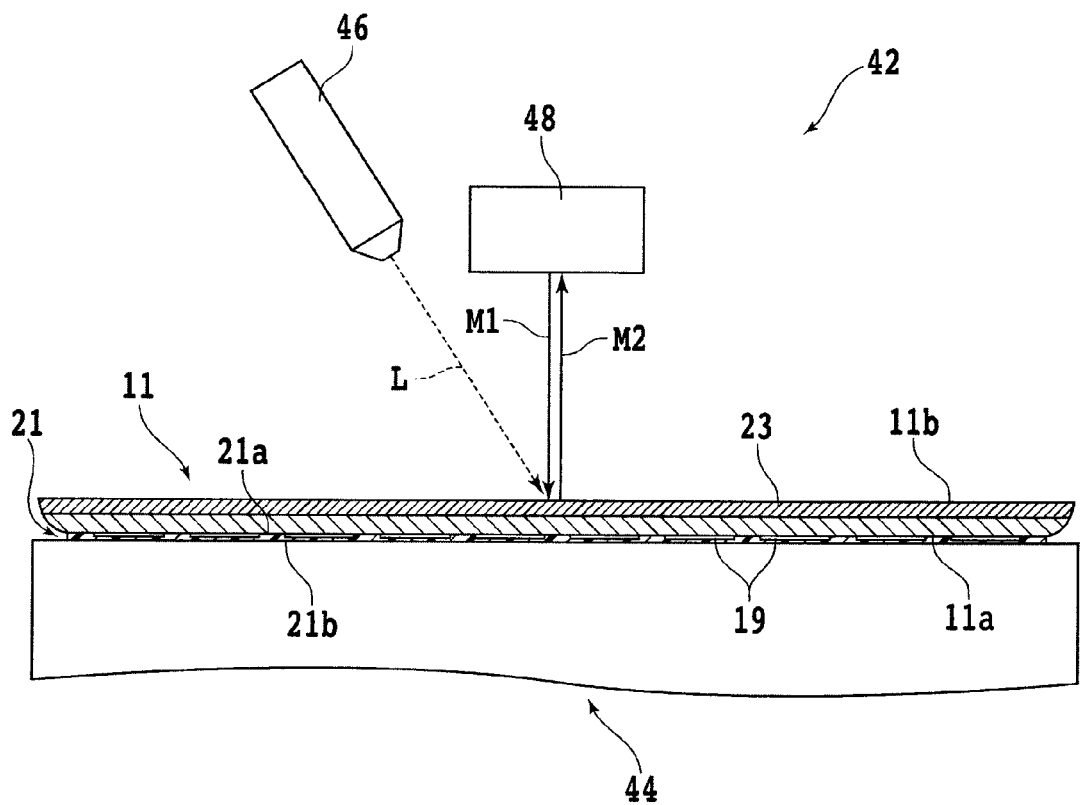
FIG. 4 is a partially sectional side view schematically showing an evaluation method of the device wafer according to an embodiment.

Next, the evaluation method for evaluating the gettering capability of the above-described device wafer 11 will be described. FIG. 4 is a partially sectional side view schematically showing the evaluation method of a device wafer according to the present embodiment. As shown in FIG. 4, the evaluation method of the present embodiment is carried out by using an evaluation device 42. As shown in FIG. 4, the evaluation device 42 includes a placement table 44 on which the device wafer 11 is placed. Above the placement table 44, a laser beam irradiating unit 46 that irradiates the device wafer 11 with a pulse laser beam (excitation light) L having a predetermined wavelength (e.g. 904 nm, 532 nm, 349 nm, etc.) is positioned. Near the laser beam irradiating unit 46, a microwave transmitting/receiving unit 48 that transmits (radiates) microwaves (electromagnetic waves) M1 toward the device wafer 11 and receives microwaves (electromagnetic waves) M2 reflected by the device wafer 11 is disposed. By this microwave transmitting/receiving unit 48, change in the intensity of the microwaves M2 reflected by the device wafer 11 can be detected.

In the evaluation method according to the present embodiment, first, the device wafer 11 is placed on the upper surface of the placement table 44, with the side of the back surface 11b of the device wafer 11 exposed to the upper side. Next, the microwaves (electromagnetic waves) M1 are transmitted (radiated) from the microwave transmitting/receiving unit 48 toward the back surface 11b of the device wafer 11. When, in this state, the region irradiated with the microwaves M1 is irradiated with the pulse laser beam L from the laser beam irradiating unit 46, excess carriers (electrons, holes) are generated on the side of the back surface 11b of the device wafer 11 and the reflectance of the microwaves M1 increases. That is, the intensity of the microwaves M2 received by the microwave transmitting/receiving unit 48 becomes higher. Thereafter, during the period when the pulse laser beam L is not radiated, the reflectance of the microwaves M1 gradually decreases in association with the recombination of the carriers. That is, the microwaves M2 are gradually damped.

As a result of strenuous studies, the present inventor has found such a relationship that the lifetime of the carriers generated by the irradiation with the pulse laser beam L (time from generation of carriers to recombination) is shorter when the gettering capability of the gettering layer 23 is higher. Then, the present inventor has completed the present invention based on an idea that the gettering capability can be evaluated by measuring the damping time of the microwaves M2 corresponding to the lifetime of the carriers. Specifically, the damping time of the microwaves M2 about the device wafer 11 as the evaluation target is measured and the gettering capability is evaluated by comparing this damping time with a predetermined reference time. As the reference time, the damping time of the microwaves M2 about a wafer in which the gettering layer 23 is not formed (bare wafer) can be used for example.

If this reference time is used and the wavelength of the pulse laser beam L is set to 904 nm, the device wafer 11 whose damping time is equal to or shorter than 94% of the reference time is evaluated as having gettering capability. Furthermore, if the wavelength of the pulse laser beam L is set to 532 nm, the device wafer 11 whose damping time is equal to or shorter than 75% of the reference time is evaluated as having gettering capability. Moreover, if the wavelength of the pulse laser beam L is set to 349 nm, the device wafer 11 whose damping time is equal to or shorter than 45% of the reference time is evaluated as having gettering capability. However, the wavelength of the pulse laser beam L that can be used for this evaluation method is not limited to the above-described 904 nm, 532 nm, and 349 nm.

Furthermore, it is also possible to evaluate the flexural strength of the device wafer 11 by a similar method. If the above-described reference time is used and the wavelength of the pulse laser beam L is set to 904 nm, the device wafer 11 whose damping time is equal to or longer than 85% of the reference time is evaluated as having favorable flexural strength. Furthermore, if the wavelength of the pulse laser beam L is set to 532 nm, the device wafer 11 whose damping time is equal to or longer than 55% of the reference time is evaluated as having favorable flexural strength. Moreover, if the wavelength of the pulse laser beam L is set to 349 nm, the device wafer 11 whose damping time is equal to or longer than 20% of the reference time is evaluated as having favorable flexural strength. Also in the case of evaluating the flexural strength of the device wafer 11, the pulse laser beam L having a different wavelength from the above-described 904 nm, 532 nm, and 349 nm can be used.

Next, a description will be made about an experiment carried out in order to confirm the validity of the above-described evaluation.

(Experiment)

In this experiment, the above-described damping time, the resistance against metal contamination, and the flexural strength were checked about the device wafers 11 in which the gettering layer 23 was formed under conditions different from each other (condition 1 to condition 10). The wavelengths of the pulse laser beam L radiated to the device wafers 11 were three kinds of wavelengths, 904 nm, 532 nm, and 349 nm. The experimental result obtained when the wavelength of the pulse laser beam L was 904 nm is shown in table 1. The experimental result obtained when the wavelength of the pulse laser beam L was 532 nm is shown in table 2. The experimental result obtained when the wavelength of the pulse laser beam L was 349 nm is shown in table 3. In each table, "OK" represents the favorable state and "NG" represents the defective state. Furthermore, in each table, the experimental result of a wafer in which the gettering layer 23 was not formed (bare wafer) is shown as a reference.

TABLE 1

|  | Damping Time (%) | Metal Contamination | Flexural Strength |
| --- | --- | --- | --- |
| Reference | 100 | NG | OK |
| Condition 1 | 87.4 | OK | OK |
| Condition 2 | 88.46 | OK | OK |
| Condition 3 | 88.46 | OK | OK |
| Condition 4 | 91.58 | OK | OK |
| Condition 5 | 90.24 | OK | OK |
| Condition 6 | 89.79 | OK | OK |
| Condition 7 | 94.04 | NG | OK |
| Condition 8 | 90.13 | OK | OK |
| Condition 9 | 105.12 | NG | OK |
| Condition 10 | 84.8 | OK | NG |

TABLE 2

|  | Damping Time (%) | Metal Contamination | Flexural Strength |
| --- | --- | --- | --- |
| Reference | 100 | NG | OK |
| Condition 1 | 73.34 | OK | OK |
| Condition 2 | 61.02 | OK | OK |
| Condition 3 | 60.52 | OK | OK |
| Condition 4 | 62.88 | OK | OK |
| Condition 5 | 62.76 | OK | OK |
| Condition 6 | 60.14 | OK | OK |
| Condition 7 | 75.43 | NG | OK |
| Condition 8 | 57.65 | OK | OK |
| Condition 9 | 125.03 | NG | OK |
| Condition 10 | 54.72 | OK | NG |

TABLE 3

|  | Damping Time (%) | Metal Contamination | Flexural Strength |
| --- | --- | --- | --- |
| Reference | 100 | NG | OK |
| Condition 1 | 21.59 | OK | OK |
| Condition 2 | 30.75 | OK | OK |
| Condition 3 | 35.21 | OK | OK |
| Condition 4 | 43.42 | OK | OK |
| Condition 5 | 42.95 | OK | OK |

TABLE 3-continued

|  | Damping Time (%) | Metal Contamination | Flexural Strength |
|---|---|---|---|
| Condition 6 | 42.01 | OK | OK |
| Condition 7 | 45.12 | NG | OK |
| Condition 8 | 36.38 | OK | OK |
| Condition 9 | 114.7 | NG | OK |
| Condition 10 | 19.38 | OK | NG |

From the respective tables, it can be confirmed that the above-described evaluation is valid. For example, to ensure both the gettering capability and the flexural strength, the device wafer 11 is processed to satisfy the following condition. Specifically, when the wavelength is 904 nm, the damping time is 85% to 94% of the reference time. When the wavelength is 532 nm, the damping time is 55% to 75% of the reference time. When the wavelength is 349 nm, the damping time is 20% to 45% of the reference time.

As described above, in the evaluation method of the device wafer according to the present embodiment, by utilizing such a relationship that the lifetime of excess carriers generated by irradiation with the pulse laser beam (excitation light) L is shorter when the gettering capability of the gettering layer 23 is higher, the gettering capability is evaluated on the basis of the damping time of the microwaves (reflected electromagnetic waves) M2 equivalent to the lifetime of the carriers. Therefore, the gettering capability can be evaluated without having to contaminate the device wafer 11 with metal elements differently from the evaluation method of the related art.

The present invention is not limited to the description of the above embodiment and can be carried out with various changes. For example, in the above embodiment, the damping time of the microwaves M2 about a wafer in which the gettering layer 23 is not formed (bare wafer) is used as the reference time. However, the reference time can be arbitrarily changed. For example, the damping time of the microwaves M2 about the device wafer 11 whose gettering capability is optimized may be used as the reference time. Furthermore, in the above embodiment, the microwave transmitting/receiving unit 48 integrally including the transmitting part that transmits (radiates) the microwaves M1 toward the device wafer 11 and the receiving part that receives the microwaves (electromagnetic waves) M2 reflected by the device wafer 11 is described. However, the transmitting part and the receiving part of the microwave transmitting/receiving unit may be separate parts.

The present invention is not limited to the details of the above described preferred embodiment. The scope of the invention is defined by the appended claims and all changes and modifications as fall within the equivalence of the scope of the claims are therefore to be embraced by the invention.

What is claimed is:

1. An evaluation method of a device wafer on which a plurality of devices are formed on a front surface and inside which a gettering layer is formed, the evaluation method comprising:
   radiating electromagnetic waves toward a back surface of the device wafer and radiating excitation light to generate excess carriers; and
   determining gettering capability of the gettering layer formed in the device wafer on the basis of a damping time of reflected electromagnetic waves.

2. The evaluation method of a device wafer according to claim 1, wherein
   a wavelength of the excitation light is 904 nm, and
   the device wafer in which the damping time is equal to or shorter than 94% of the damping time in a wafer inside which a gettering layer is not formed is determined to have gettering capability.

3. The evaluation method of a device wafer according to claim 1, wherein
   a wavelength of the excitation light is 532 nm, and
   the device wafer in which the damping time is equal to or shorter than 75% of the damping time in a wafer inside which a gettering layer is not formed is determined to have gettering capability.

4. The evaluation method of a device wafer according to claim 1, wherein
   a wavelength of the excitation light is 349 nm, and
   the device wafer in which the damping time is equal to or shorter than 45% of the damping time in a wafer inside which a gettering layer is not formed is determined to have gettering capability.

* * * * *